US005633910A

United States Patent [19]

Cohen

[11] Patent Number: 5,633,910
[45] Date of Patent: May 27, 1997

[54] OUTPATIENT MONITORING SYSTEM

[76] Inventor: Kopel H. Cohen, 2362 Harbour Oaks Dr., Longboat Key, Fla. 34228

[21] Appl. No.: 305,108

[22] Filed: Sep. 13, 1994

[51] Int. Cl.$^6$ .................................................. H04M 11/00
[52] U.S. Cl. ............................ 379/38; 379/88; 379/97
[58] Field of Search ........................ 379/38, 97, 98, 379/96, 100, 93, 88, 39, 40, 102, 104, 105

[56] References Cited

U.S. PATENT DOCUMENTS

| | | |
|---|---|---|
| 3,727,190 | 4/1973 | Vogelman et al. . |
| 3,774,164 | 11/1973 | Osterberg et al. . |
| 3,882,277 | 5/1975 | De Pedro et al. . |
| 3,972,320 | 8/1976 | Kalman . |
| 4,068,097 | 1/1978 | Verriest . |
| 4,296,756 | 10/1981 | Dunning et al. . |
| 4,337,377 | 6/1982 | Van Riper et al. . |
| 4,346,697 | 8/1982 | Cohen . |
| 4,458,693 | 7/1984 | Badzinski et al. . |
| 4,712,562 | 12/1987 | Ohayon et al. . |
| 4,751,726 | 6/1988 | Hepp et al. . |
| 4,803,625 | 2/1989 | Fu et al. . |
| 4,843,377 | 6/1989 | Fuller et al. ........................ 379/38 |
| 4,858,121 | 8/1989 | Barber et al. . |
| 4,883,064 | 11/1989 | Olson et al. . |
| 5,036,852 | 8/1991 | Leishman . |
| 5,038,800 | 8/1991 | Oba . |
| 5,065,315 | 11/1991 | Garcia . |
| 5,099,424 | 3/1992 | Schneiderman . |
| 5,107,831 | 4/1992 | Halpern et al. . |
| 5,142,484 | 8/1992 | Kaufman et al. . |
| 5,159,317 | 10/1992 | Brav . |
| 5,172,698 | 12/1992 | Stanko . |
| 5,179,587 | 1/1993 | Bock et al. . |
| 5,204,670 | 4/1993 | Stinton . |
| 5,207,580 | 5/1993 | Strecher . |
| 5,253,285 | 10/1993 | Alheim . |
| 5,289,521 | 2/1994 | Coleman et al. . |
| 5,289,531 | 2/1994 | Levine ........................... 379/104 |
| 5,305,238 | 4/1994 | Starr, III et al. . |
| 5,321,618 | 6/1994 | Gessman . |
| 5,377,258 | 12/1994 | Bro ............................... 379/88 |

OTHER PUBLICATIONS

L. Baer, et al., *Automated Telephone Screen Survey For Depression*, JAMA, Jun. 28, 1995, vol. 273, No. 24, pp. 1943–1944.

Paper entitled "Telecommunications in Managed Self Care", by Farrokh Alemi, Ph.D., presented at 17th Annual Symposium on Computer Applications in Medical Care, Oct. 31, 1993.

*Primary Examiner*—Stella Woo
*Attorney, Agent, or Firm*—Kenyon & Kenyon

[57] ABSTRACT

A patient monitoring system. A patient has access to a touch-tone telephone that has keys. The telephone is operated by a patient to generate DTMF tones. A central monitoring system is coupled to the touch-tone telephone. The central monitoring system generates questions concerning a health condition of the patient for the patient to answer using the keys of the touch-tone telephone. The central monitoring system stores answers to the questions for later retrieval. The central monitoring system include a DTMF modem decoder for receiving and decoding DTMF tones generated by the patient using the touch-tone telephone and transmitted to the central monitoring system. The DTMF tones represent the health condition of the patient. A computer processor is coupled to the DTMF modem decoder. A voice generator is also coupled to the computer processor and generates voice output under the control of the computer processor. The voice output is transmitted to the touch-tone telephone. A database is coupled to the computer processor, storing a patient record reflecting the health condition of the patient and also storing the questions concerning the health condition of the patient.

35 Claims, 6 Drawing Sheets

OUTPATIENT MONITORING SYSTEM

FIELD OF INVENTION

The present invention is directed to a computer-implemented method and system for monitoring the health status of patients, and in particular, a method and system utilizing a telecommunications system and Dual Tone Multifrequency ("DTMF") decoder to monitor the health status of outpatients.

COPYRIGHT NOTICE

A portion of the disclosure of this patent document contains material which is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

BACKGROUND OF THE INVENTION

Much of the cost of providing health care is associated with time spent by medical personnel consulting with patients. Whereas equipment is relatively easy to procure, it is costly to provide the extensive training and experience required by health care professionals to enable them to provide quality health care. The growing demand for medical services at a reasonable cost has placed unprecedented demands on the health-care provider.

An outpatient usually resides at a location away from a health care provider. For example, an outpatient typically resides at home and not in the hospital where his or her doctor may have an office. Thus, the health care provider has far less opportunity to monitor the health status of an outpatient patient on day to day basis. Moreover, an outpatient may be required to see a doctor on a regular basis, often for simple and routine tests. In such a case, the outpatient must travel to the doctor's office or to a hospital, wait to be seen by the relevant health care provider, have the tests performed, and travel home. This inconvenient way of monitoring the health of an outpatient often does not assist the outpatient in the recovery process.

In short, patients in a hospital are regularly monitored. However, outpatients often do not receive this same level of health care.

A system is needed that will help close the gap between the level of care received by hospitalized patients and non-hospitalized patients who must visit the doctor or other health care provider for treatment. It would be advantageous if a health care provider could regularly monitor the health status of patients, including outpatients, without requiring these patients to physically travel to and make an appointment with the health care provider unless it is absolutely necessary to do so.

Many of the advantages of a remote outpatient monitoring system would be negated if the system were exceedingly costly or complex to use. Existing outpatient monitoring systems require the patient to use expensive equipment that is unfamiliar to the patient and complex to use. For example, many existing monitoring systems involve connecting sensors to the patient to monitor vital signs, such as blood pressure or temperature. Other systems require that one or more sensors be physically implanted into the patient's body.

Moreover, these systems often have a dedicated use, for example, they can only be used to monitor one or two conditions of the patient. These systems are less flexible, each being directed towards reporting a fairly narrow range of data to the health care provider, often on an intermittent basis. For example, one system may be capable of transmitting only heart rate and blood pressure; another may monitor and transmit sounds from implanted heart valves; yet another may be needed to monitor and transmit "biologic signals."

For example, U.S. Pat. No. 4,712,562 to Ohayon et al. describes a system to monitor the blood pressure and heart rate of an outpatient that requires the outpatient be provided with a special device that can take blood pressure and heart rate readings, store these readings, and later generate signals for transmission. These signals represent the stored readings and the identity of the patient. In such a system, the outpatient must be supplied with a measurement, storage and signal generating device that is programmed for use by that particular outpatient only.

U.S. Pat. No. 5,172,698 to Stanko describes a dedicated telephonic pacemaker monitoring device that has four electrode touch pads that can detect pacemaker signals or a patient's pulse and transit the detected information over a telephone line.

U.S. Pat. No. 3,882,277 to DePedro et al. describes a portable battery-powered EKG signal detector and transmitter. EKG signals can be transmitted over a telephone link to monitoring equipment at another location.

U.S. Pat. No. 4,068,097 to Verriest describes a system that requires a specially adapted telephone set that is capable of direct communication with a central monitoring station without the handset being lifted.

U.S. Pat. No. 4,337,377 to Van Riper et al. describes an apparatus to monitor biologic signals of a patient from a telephone handset. This system requires the patient to carry a special unit that must be coupled to the telephone handset.

In the above systems, the patient has to obtain and use an electronic device capable of taking readings and transmitting data over a telephone line, often using complex communication protocols. Many of these devices have a dedicated use, i.e., are programmed for use by one patient only or are programmed for use for one set of measurements only.

Thus, there is a need for a system for remotely monitoring the health status of patients that does not require special training or complex equipment that is likely to be expensive. In particular, there is a need for a monitoring system that does not require that the patient be provided with any electronic equipment, thus allowing the patient to use communications equipment that the patient already has in his or her own home.

Further, there is a need for a single system that is capable of being adapted to an individual's evolving physical condition. Each patient may have different conditions that require monitoring. For example, for one patient, pulse information may be important, for another, blood pressure, and for a third patient, temperature. The health care provider needs a single system to easily monitor all conditions of all patients.

Further, as a patient's condition improves, some information may not be needed. Existing systems are not flexible and cannot easily be adapted for each patient's differing and evolving conditions.

Existing monitoring systems concentrate on obtaining information relating to physical conditions, such as blood pressure, pulse, EKG and the like. Often, for example, when a patient is taking medicine or has a psychological problem, the health care provider must additionally monitor other factors, such as how well a patient sleeps, whether the patient feels drowsy or depressed, and whether the patient has an appetite. Existing monitoring systems do not enable health care providers to remotely monitor psychological and other related conditions of a patient.

SUMMARY OF THE INVENTION

The present invention is directed to a method and system for remotely monitoring the health status of patients, in particular outpatients, using telecommunications hardware systems already likely to exist in a patient's home, such as, for example, a telephone or personal computer with a modem.

The representative embodiment of the present invention can be regarded as having two subsystems, namely, a central monitoring subsystem and a patient subsystem.

The central monitoring subsystem receives, stores and processes health information provided by one or more patients, and generates periodic reports for the relevant health care providers. Typically, the central monitoring subsystem is located in a central location so as to be accessible by telephone to all patients who require monitoring. Further, the central monitoring subsystem is often located so as to be readily available to the health care providers using the system, for example, in a hospital or doctor's office. However, since the central monitoring subsystem could be used and shared by a number of doctors and hospitals, it could be located in a remote location, accessible by modem, WAN or the Internet, so that relevant reports could be distributed electronically to the relevant health care providers who require such reports.

In the representative embodiment, the central monitoring subsystem comprises at least one computer processor coupled to a telecommunications line by (for example) a modem capable of interpreting dual tone multifrequency (DTMF) signals, software to control the operation of the computer processor, a database and DBMS to store information and generate reports regarding the health status of patients, and a voice generator capable of generating voice instructions understandable by humans over the telecommunications system. Optionally, the central monitoring subsystem can include a printer for printing the generated reports. Further, the computer processor can be part of a local area network (LAN).

The patient subsystem enables a patient to transmit information about the patient's health status to the central monitoring subsystem. There is likely to be more than one patient being monitored at a time. Thus, in the representative embodiment, each patient will have (or have access to) a patient subsystem. Typically, the patient subsystem will be located in the home or office of the patient. It is noted, however, that (depending on the condition of the patient) the patient requires no special equipment to successfully utilize the capabilities of the present invention. The patient may use, for example, any touch-tone telephone as the patient subsystem.

In the representative embodiment, the patient subsystem comprises an instrument capable of receiving instructions from the central monitoring subsystem and capable of sending data to the central monitoring subsystem. Typically, the patient subsystem comprises a touch tone telephone coupled to a telephone line. For more sophisticated users, the patient subsystem may be a computer and modem.

Thus, in a typical embodiment of the present invention, the patient needs only a touch tone telephone. This is the same kind of telephone already owned by most households. Further, the telephone used in the present invention need not be in addition to the one used for everyday calls; nor is any additional telephone line required. (More sophisticated patients can use a computer with a modem to communicate with the central monitoring subsystem.) Thus, there will be no additional cost to the patient for special equipment. Nor does the health care provider acquire expensive equipment according to the present invention. In a representative embodiment, the central monitoring subsystem includes a general purpose, off-the-shelf, home computer, software, a voice generator, and a DTMF modem. These components are relatively simple devices commonly available. As is known in the art, the DTMF modem is capable of receiving the dual tones generated by a touch-tone telephone keypad that have been transmitted over the telephone line and translating the tones into characters recognizable by the computer processor. The equipment used in the representative embodiment of the present invention is readily available commercially, is inexpensive, and is easy to use.

In the representative embodiment, the computer processor of the central monitoring subsystem is capable of receiving and decoding information from patients received via the DTMF modem. Patients communicate with the central monitoring subsystem using a touch tone telephone or a computer with a modem. The information received and decoded at the central monitoring subsystem is stored in the database. The computer processor makes decisions based upon the information received and other information previously stored in the database.

A representative embodiment of the present invention operates as follows: A health care provider supplies a patient with a telephone number. When dialing this number from a telephone, the patient is connected to the central monitoring subsystem. The computer processor of the central monitoring subsystem, controlled by software, sends information (for example, instructions or questions) to the patient. Typically, these instructions or questions will be communicated orally to the patient, for example, they will be generated by the voice generator. The computer processor asks the patient to identify himself or herself, for example, by entering an alphanumeric identification or patient code using the touch tone keypad. (E.g., the patient presses the keys corresponding to the assigned patient code on the keypad on the patient's touch-tone telephone. It is noted that there can be added security measures, such as passwords or keycodes that may also have to be entered by the patient.) The patient code is received at the central monitoring subsystem, decoded, and the patient's record is retrieved from the database.

The patient's record typically comprises information about the patient's medical condition including information previously entered by the patient using the system of the present invention. Using the information in the patient's record, the central monitoring subsystem can generate questions that the patient must respond to so that relevant information can be entered by and received from the patient.

Additionally, or in the alternative, the patient can be provided with a printed chart of questions that the patient must answer prior to calling the central monitoring subsystem. Each patient may have a chart that corresponds to that patient's individual condition. The patient fills in the answers to the questions on the chart. The patient communicates by telephone with the central monitoring subsystem and enters the patient code (and, if required, a chart code identifying the chart that the patient is using). The central monitoring subsystem will then ask the patient for each answer that the patient has entered on the chart. The patient answers using the touch tone keypad. The chart that the patient uses may be that of the type described in U.S. Pat. No. 4,346,697 entitled "Method For Treating Depression and Other Maladies By Means Of Patient-Created Symptom Graphs", which is expressly incorporated herein by reference.

Thus, in short, after the patient has entered the patient code, the central monitoring subsystem asks the patient one or more questions, which the patient answers using keys on the patient's touch-tone telephone. The patient is instructed to respond by entering information through the keypad of the telephone, such as selecting the best answer by touching its corresponding key. The computer processor of the central monitoring subsystem records and processes the patient's response. The computer processor may select the next query by consulting the database and considering the patient's response to previous questions. The central monitoring subsystem asks the patient the next question, records and processes the response, and so on. This process continues until sufficient information has been obtained from the patient, and then the central monitoring subsystem issues final instructions and terminates the call.

When each call is terminated, or at regular intervals, the central monitoring subsystem will produce reports for each of the health care providers utilizing the present invention. Typical reports that may be generated are patient status reports, reports of patients who have not entered information for a recent period and reports of patients who should be called in for an appointment, for example, due to a change in condition or because of unsatisfactory progress. In a representative embodiment, the central monitoring subsystem can quickly alert the relevant health care provider in the event of an exigency revealed in the data gathered from the patient.

Thus, based upon the reports, the health care provider can decide upon a course of action, including whether a personal consultation with the patient is necessary, whether the patient should be contacted by telephone, or whether a change in medication is needed.

The central monitoring subsystem can include an artificial intelligence expert system that intelligently questions each patient according to that patient's needs, and intelligently assists doctors in determining which patients require a physical consultation.

The database of the central monitoring subsystem can be the same database used by the health care provider to store patient records, such as name, address, billing information and the like.

In an alternative embodiment, the central monitoring subsystem can receive and interpret information in voice format from a patient. For example, the patient may be asked to identify himself or herself. Instead of entering a patient code, the patient can speak his or her name into the telephone, which is received by the central monitoring subsystem and compared with voice fingerprints previously stored, thus providing a secure way of identifying patients.

Additionally, the present invention can be adapted so that patients can also provide information to the central monitoring subsystem by means of a computer, such as a personal computer, and modem, of the type usually found in a home. The patient can dial up the computer processor of the central monitoring subsystem using the modem, and interactively provide answers to questions communicated over the modem by the central monitoring subsystem. In this embodiment, the questions could be presented to the patient in the format of the forms described in U.S. Pat. No. 4,346,697 referred to above.

In the representative embodiment, the patient is charged for use of the present invention. For example, the central monitoring subsystem may only be accessible via a "1-900" telephone number, where the patient is charged a premium rate per minute of call. Alternatively, the central monitoring subsystem can record the number of calls made by the patient, and charge the patient a fixed rate per call. However, it is recognized that the present invention can be provided free of charge to patients, for example, as a service by a doctor or through other health care providers, such as HMOs, to attract new patients or customers.

In summary, the present invention provides a screening process that is significantly more efficient than the primary care systems in place today. It is less costly because it makes no demands on the time and expertise of the health-care provider for the purpose of gathering data on the health and status of patients. Rather, the provider uses his time and expertise far more effectively by analyzing the raw data that, prior to the invention, the health care provider would have had to gather manually.

The patient does not have to visit a hospital or occupy a hospital bed for regular monitoring of health status, but rather, is able to provide such information conveniently from any touch-tone telephone. Needed hospital beds are made available and unnecessary office visits are avoided, saving both the patient and health care provider time and money.

The present invention can be used to report and analyze more than just the vital signs and physiological characteristics of a patient. For example, the present invention can also be used to report and analyze emotional, mental and psychological characteristics of a patient, and indications of general well being. For example, when the patient is taking medication, the present invention can be used in the treatment of depression and other maladies. It can also be used to carry out an extensive psychological evaluation of a patient on an on-going basis.

Also, unlike the other existing systems, the present invention is adaptive. That is, it can, if required, actively decide what information is needed from a patient based upon information received from the patient. This gives the present invention a degree of flexibility and value to the physician that is superior to that afforded by other monitoring systems.

The present invention is capable of meeting the conflicting demands of providing higher quality health care at lower cost. It is easy to use, is economical, and multiplies the utility of the medical professional in the health care system by making more efficient use of time and expertise. It also reduces the cost of medical care by allowing the health care provider to regularly obtain certain information while the patient is at home. By increasing the number of inpatients who can be treated on an outpatient basis, the present invention allows hospital beds to be used more efficiently for those with more severe conditions.

DETAILED DESCRIPTION

Figure 1:
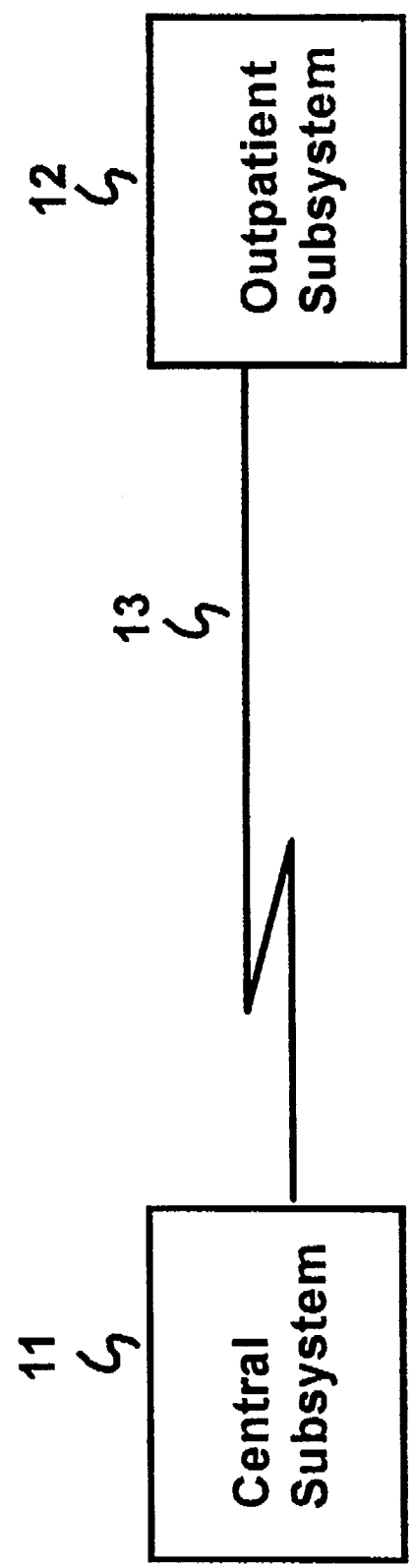
FIG. 1 is a block diagram of the two main subsystems of the present invention.

Referring now to the drawings, and initially FIG. 1, there is illustrated a representative embodiment of an outpatient monitoring system comprising two subsystems, namely, a central monitoring subsystem 11 and an outpatient subsystem 12. The central monitoring subsystem 11 is located so as to be readily accessible to one or more health care providers. The outpatient subsystem 12 is located so as to be readily accessible to an outpatient. The central monitoring subsystem 11 and the outpatient subsystem 12 are coupled by a telecommunications system 13, such as, for example, a public telephone network.

As used herein, the term "provider" or "health care provider" includes doctors, psychologists, HMOs, hospitals, health clinics, managed care entities, and the like.

FIG. 1 shows only one outpatient subsystem 12. However, the present invention is designed for use by many patients. Thus, there will be many outpatient subsystems 12, for example, one for each patient, each coupled to the central monitoring subsystem 12 via the telecommunications system 13.

Figure 2:
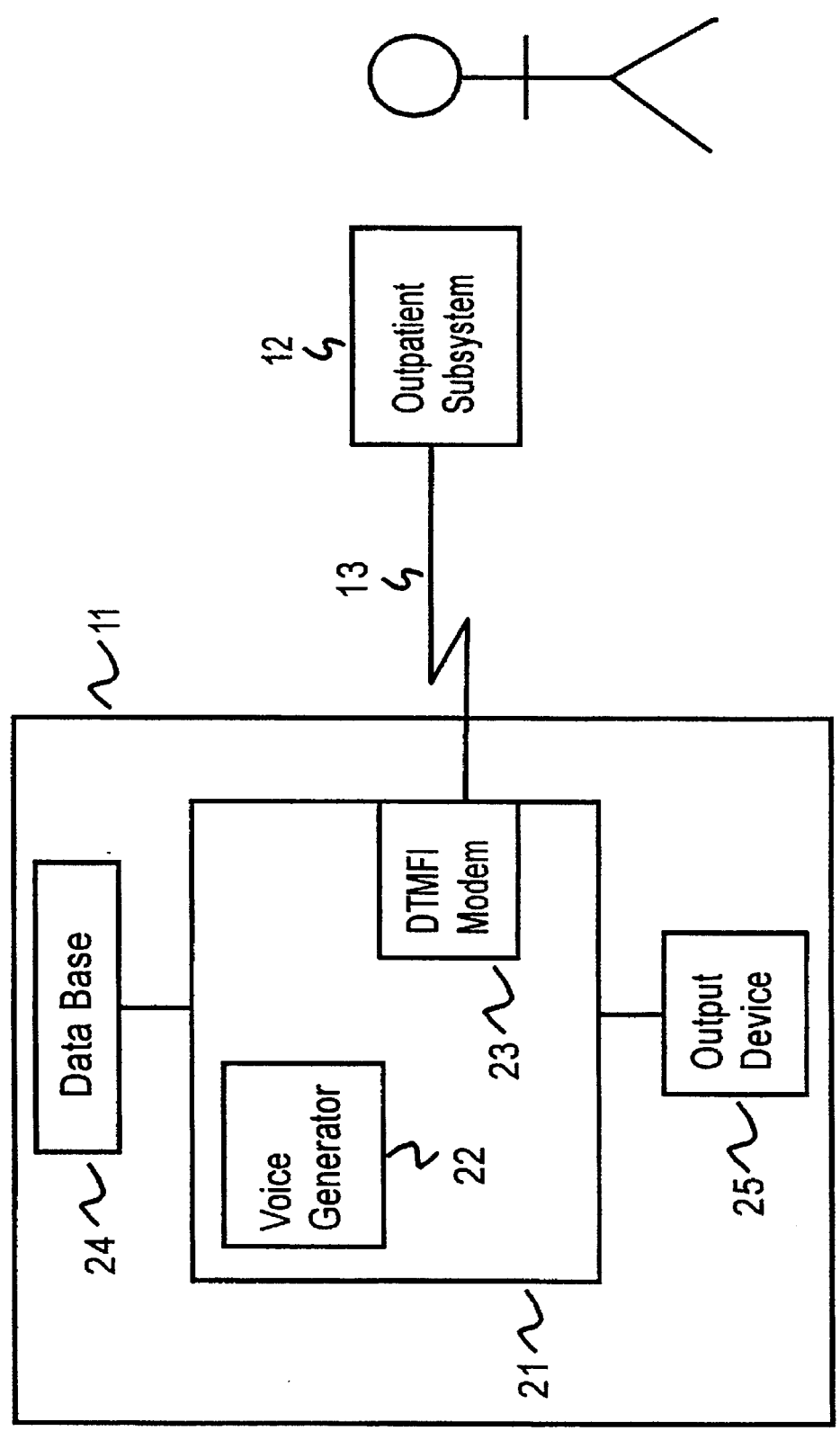
FIG. 2 is a block diagram illustrating in further detail the components of the two subsystems of FIG. 1.

Referring now to FIG. 2, the central monitoring subsystem 11 of the representative embodiment of the present invention comprises a computer processor 21, such as, for example, an Apple Macintosh computer, a SUN brand workstation or an IBM personal computer with a 486 Intel processor. The computer processor includes (or is coupled to) a voice generator 22 and a dual tone multifrequency (DTMF) modem 23. The computer processor can also access a database 24, storing, for example, patient information and health status information that is input by a user, such as, for example, a patient. The computer processor 21 is also coupled to an output device 25, such as a monitor or a printer. The voice generator 22 and the DTMF modem 23 are coupled to the telecommunications system 13.

The computer processor 21 is capable of executing software programs, such as DBMS programs and other programs capable of carrying out the operations involved in patient monitoring. The computer processor 21, in conjunction with the software programs, is capable of actuating the voice generator 22, and can receive information from a patient via the DTMF modem 23.

The outpatient subsystem 12 of the representative embodiment is a touch tone telephone capable of generating DTMF signals using the keys of the telephone's touch tone keypad. These signals are transmitted to the DTMF modem 23 over a telecommunications system 13. The DTMF modem 23, in conjunction with the computer programs, decodes the DTMF signals and stores the received information in the database 24.

In the representative embodiment, the DTMF modem 23 is a ACC303800 Sportster FAX/modem or Digicom Systems Connection's +14.4 FAX/modem, both with DTMF dialers/decoders fax and modem chips.

The database 24 in the representative embodiment is a relational database that is used to keep track of all of the patient's medical information and other patient information. The database 24 has several properties:

Access to database 24 through a full screen graphics user interface (GUI). Providers and administrators will use this interface.

The ability for the health care provider to configure personalized GUI interface screens.

Access to database 24 through a "walkthrough" interface, for which only one question at a time is asked. The patients will use this interface.

The ability for the provider to configure personalized walkthroughs.

The ability to perform queries and reports.

The ability for the provider to customize a standard report.

Medical records are be referenced by provider and patient.

Patient data is stored in form of a patient history, so that trends can be tracked and the patient monitored over a period of time.

Security features prevent unauthorized access to or modification of records.

Figure 3:
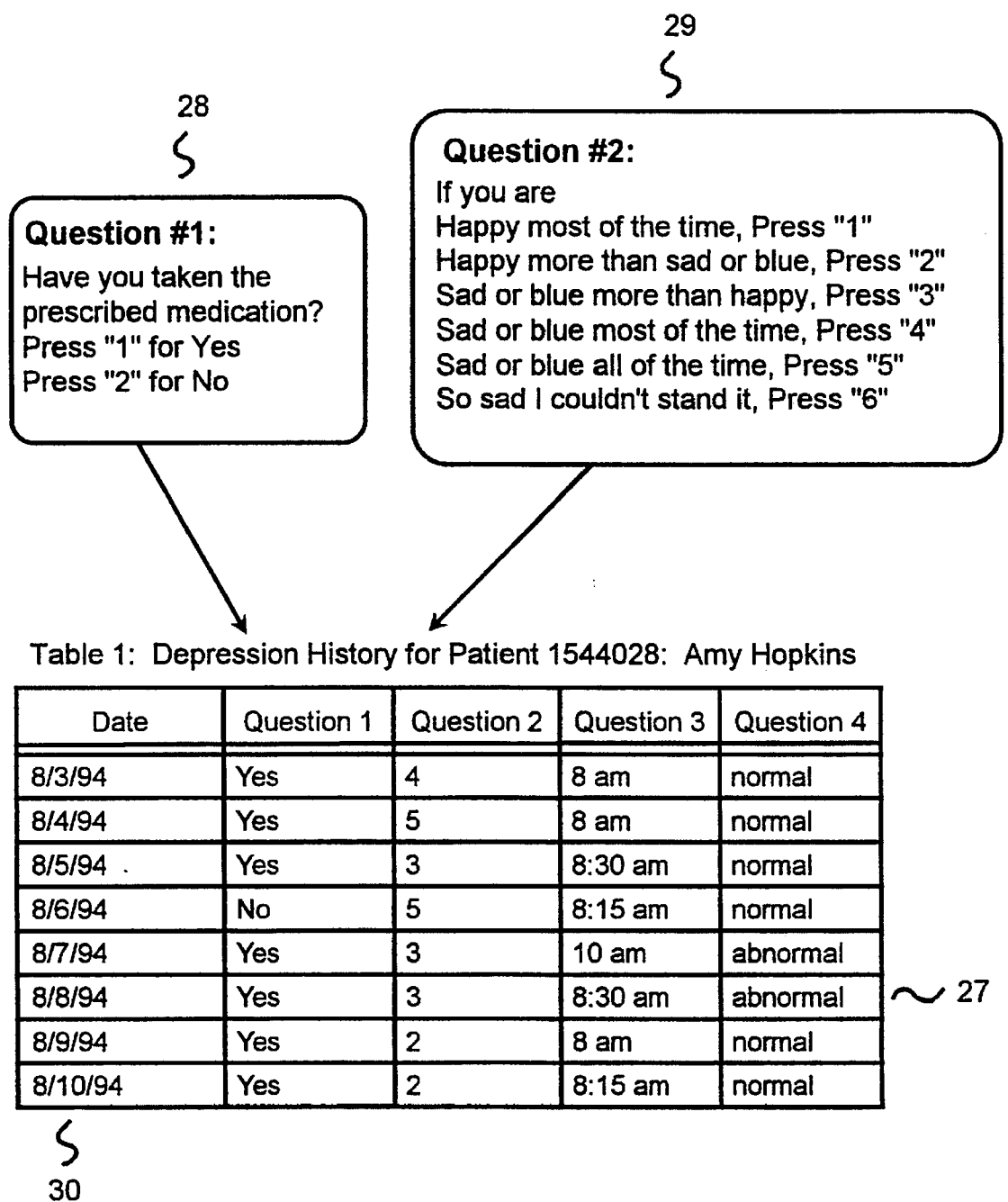
FIG. 3 is an example of a patient history, as recorded in the database of FIG. 2.

FIG. 3 illustrates a typical history table 27 for one patient. This particular patient is taking medication for depression, and has been told to phone daily to provide answers to questions. Each question is given a number. Question #1 (28) is "Have you taken the prescribed medication?". Question #2 (29) asks the patient to judge how sad or happy he or she feels. Each of these questions are asked daily, and perhaps many other questions as well. The database 24 stores this information by date, because most health care providers wish to make reports based on date. Thus ordering scheme of the database 24 is the same as the health care provider's most common requests, and generating a chronological report will not involve a huge sorting of the database 24.

The table 27 in FIG. 3 refers to a particular user, Amy Hopkins, ID number 1544028. The first column 30 specifies the date that the data was collected. The other columns list the answers to each question for the associated day. By reading down a column, you can track the history of how the answer to a question varies over the entire week 8/3/94 to 8/10/94. In the representative embodiment, each patient has a similar table, and it is possible to combine the data on several patients into a single report.

As used herein, a walkthrough is one session with a patient. In this example, a walkthrough begins when a patient starts answering questions about depression. The walkthrough ends when the patient answers the last depression question. In one embodiment of the present invention, a walkthrough flowchart defines what questions will be asked of the patient. What questions are asked depends entirely on what responses the patient gives. This is not a programming flowchart which describes how a program flows. Instead this flowchart describes how a patient walkthrough session flows.

There will be many flowcharts in the system. One may cover depression. Another may cover diabetes. Each patient will be led through the appropriate flowchart depending on their illness, in a procedure to be described later. Some patients may be led through one flowchart, and then another, if they should answer questions about more than one topic.

Figure 4:
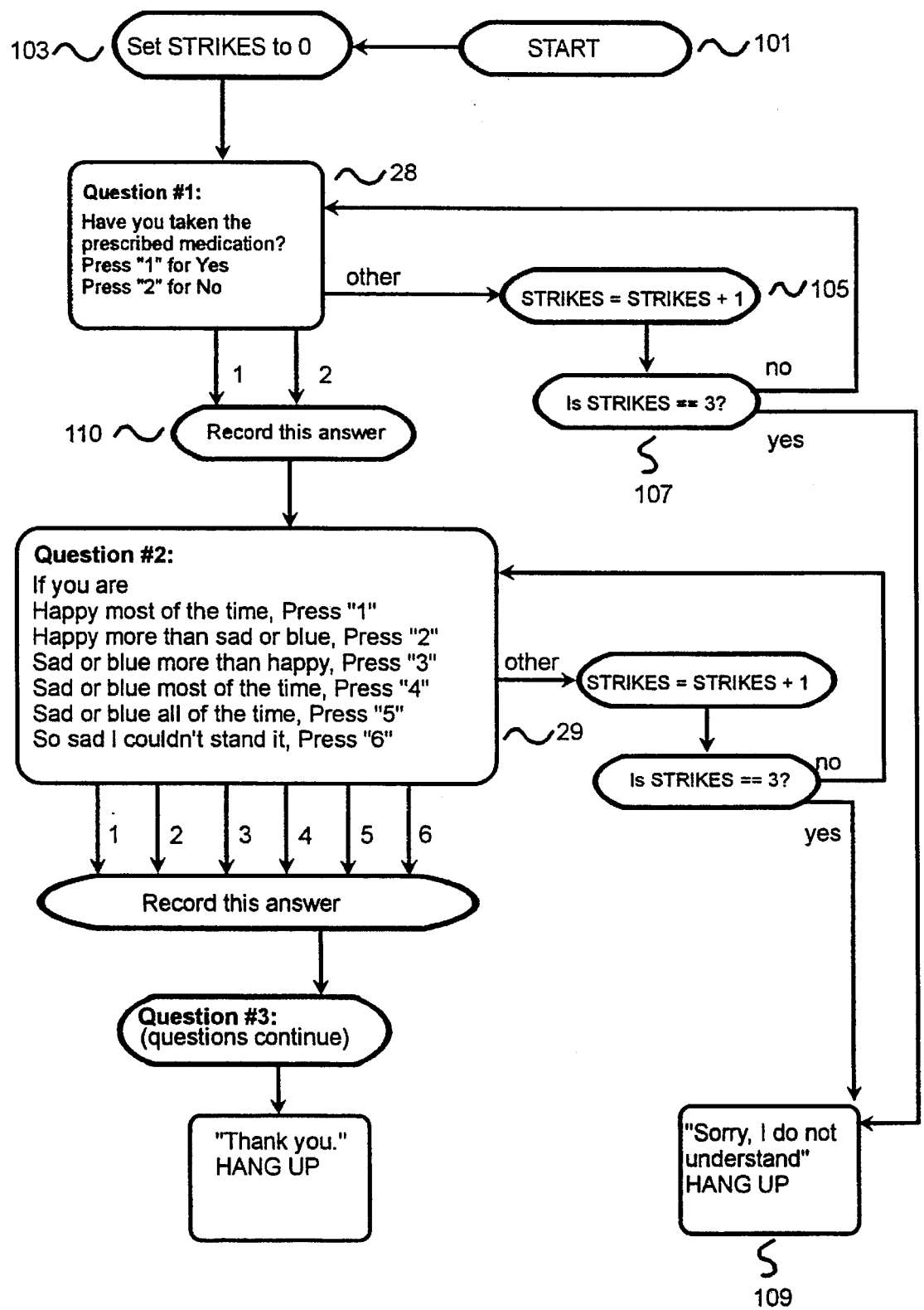
FIG. 4 is an example walkthrough flowchart.

FIG. 4 is an example of a walkthrough flowchart for depression. When the patient is to answer questions about depression, the program starts at the START cell 101. A variable called STRIKES is set (103) to keep track of the mistakes that the user has made so far. This variable will ensure that the walkthrough is completed even if the user is constantly entering bad numbers, or if some communication problem is disrupting reception.

The walkthrough can travel from one cell to another along an arrow. So after "Set Strikes to 0" (103), the next cell is the "Question #1" cell (28). The user is asked the question listed in this cell. There are several arrows leaving this cell. The arrow that is chosen is the one matching the patient's answer. For example, if the patient presses "1", then the arrow marked "1" is followed to the cell labeled "record this answer" (110), signifying that the answer is recorded in the database 24. If the patient does not press "1" or "2", then the STRIKES variable is incremented (105), and the session may be ended if too many nonsensical answers have been given (107, 109).

The walkthrough continues to the "Question #2" cell (29), and eventually, after many more questions, to the ending of this walkthrough.

In the representative embodiment, supporting modules couple the database 24 and the walkthroughs together in application. A module is a computer programming concept that represents a piece of software that performs a small, well-defined function. A software project is constructed of several modules that use each other to accomplish a task. Sometimes, all the modules for a software project are placed together inside one program. Otherwise, the modules are placed in more than one program, and these programs must talk to each other. One benefit of placing the modules for a software project in more than one program is that each program can be run on a separate computer. The resulting parallelization is usually much faster.

Figure 5:
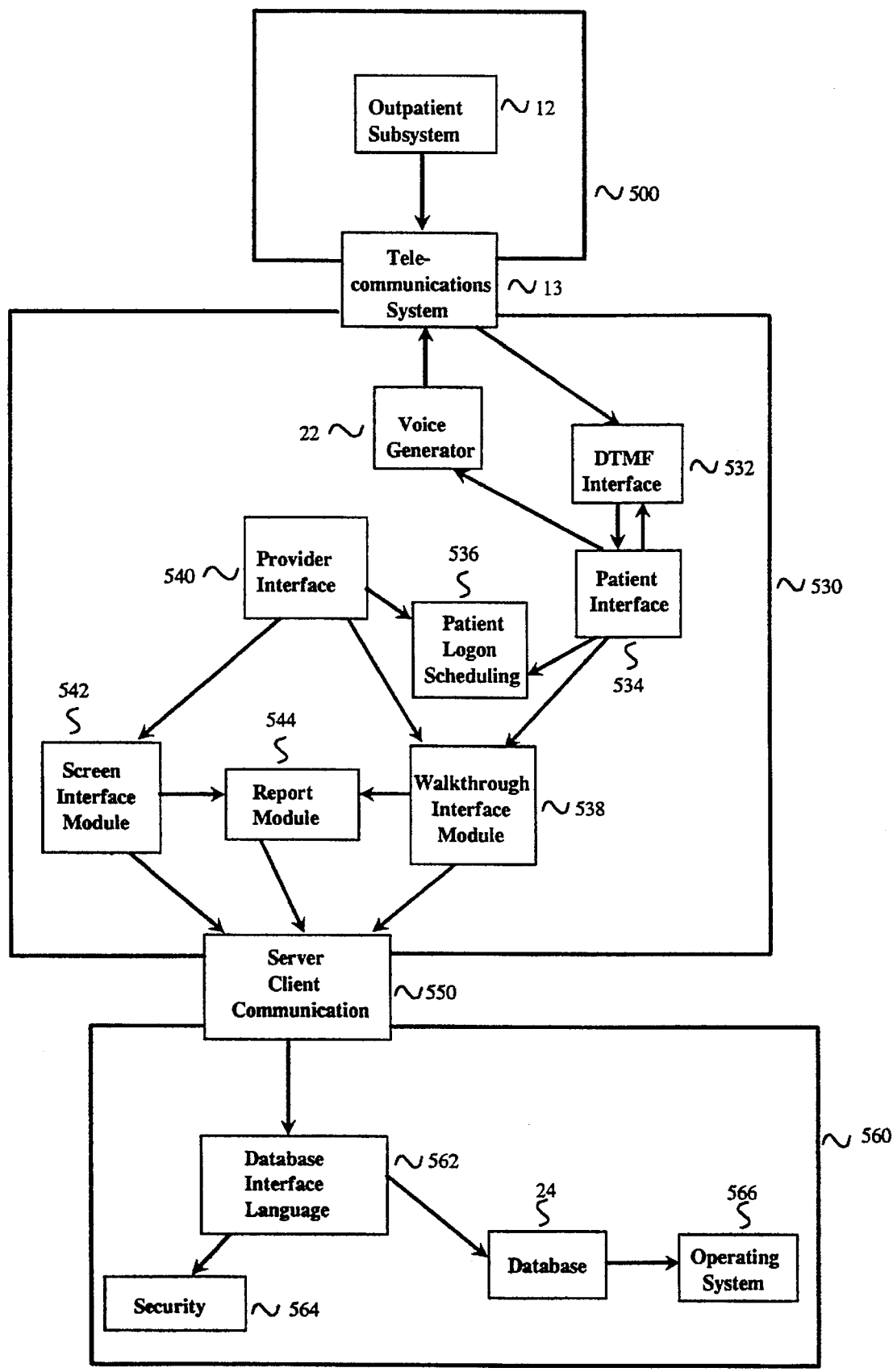
FIG. 5 is a detailed block diagram elaborating on the components of the system described in FIG. 2.

For this patient database application, there are several modules that support the functionality of the whole software project. FIG. 5 illustrates, in block diagram form, the modules used in the representative embodiment of the central monitoring subsystem 11. It is possible to describe the entire system by describing each module individually. The modules illustrated in FIG. 5 are representative only, and other configurations of modules may be used, depending on the functionality required and other design decisions.

FIG. 5 has been divided into three systems, namely, a patient system 500, an interface server 530 and a database server 560. Each system can run on a separate computer. The patient system incorporates the outpatient subsystem 12 and is coupled to a telecommunications system, as described above. The interface server 530 handles the process of getting answers from patients. It also allows access to the database 24 by the health care provider and other administrators. The database server 560 stores patient information. (The interface server 530 and the database server 560 can be regarded as comprising the central monitoring subsystem 11 of FIG. 2 above.)

Each of these separate systems can communicate over a network. For example, in the representative embodiment, the patient system 500 communicates with the interface server 530 through phone lines 13. The interface server 530 communicates with the database server through a local area network (LAN). It is also possible to combine the interface server 530 and database server 560 together into single program.

The following is a description of each module.

The outpatient system 12 is the means by which the patient communicates with the central monitoring subsystem 11, as described above. A function of the outpatient subsystem 12 is to give the patient access to the interface server 530.

The voice generator 22 speaks for the system. Whenever a question needs to be asked to the patient, the voice generator 22 translates the computer question into voice that the patient can hear.

The DTMF interface 532 alerts a patient interface 534 that a new patient has dialed in. The DTMF interface 532 picks up the phone and listens for any touchtones that are pressed. Any touchtone information is passed along to the patient interface 534. Also, the DTMF interface 532 has a timeout function, so that if the patient waits too long (perhaps 2 minutes) to press a touchtone, it will inform the patient interface 534 that no key was pressed. This insures that the system never hangs. In a similar way, the DTMF interface 532 checks to see if the patient has hung up the phone. If this happens, it also informs the patient interface 534.

The patient interface 532 finds out who the patient is, asks the Patient Logon Scheduling to find which walkthroughs the patient must go through. It then performs each walkthrough, one step at a time, calling on the walkthrough interface module 538 to interpret each walkthrough.

The following are representative examples of the functionality performed by the patient interface module 534:

Handle Patient Dialup

This procedure is called by the DTMF module 532 to handle the entire patient call by using other modules to record the patient information.

A. Execute the walkthrough "PASSWORD" using the Execute Walkthrough Algorithm, discussed below B. Get patient ID and password confirmation from Walkthrough Interface Module 538

C. If password confirmation is given:

1. Give patient ID to Patient Logon Scheduling Module 536

2. For each walkthrough in the Patient Logon Scheduling Module:

a. Receive next walkthrough name from Patient Logon Scheduling Module 536 b. Execute that walkthrough using the Execute Walkthrough Algorithm

In summary, the Handle Patient Dialup procedure is activated whenever a patient dials up. In Step A, the patient interface module 534 asks for the patient's password and identification number. These questions, like any other question in the system, can be described by a walkthrough, which is executed. In Step B, the patient interface module 534 receives information on whether the patient password is valid. If the password is not valid, then in Step C, not further action is taken. Otherwise, the password is valid, so in Step C1, the patient interface module 534 asks the patient logon scheduling module 536 to pass over all the walkthroughs this patient must go through. For example, in one embodiment, if the patient is depressed and a diabetic, then she must go through a walkthrough for depression and a walkthrough for diabetes. In Step C2, each walkthrough is executed in Execute Walkthrough procedure.

Execute Walkthrough

This procedure is called to let the patient walkthrough a specific information recording session. The Walkthrough Interface Module 538 supplies the questions. The patient interface 534 plays the questions with the voice generator and receives the answers with the DTMF interface 532.

A. Register this patient with the Walkthrough Interface Module 538

B. Ask the Walkthrough Interface Module 538 for questions

C. While the Walkthrough Interface Module 538 has more questions to ask:

1. Tell the voice generator 22 to say the question.

2. Tell the DTMF interface 532 to receive an answer

3. Pass the answer (which may be a timeout) to the Walkthrough Interface Module 538.

The Execute Walkthrough procedure uses a walkthrough to ask a patient all the appropriate questions. As discussed earlier, the path and questions asked can be determined by the answers the patient gives. Nonsensical answers may terminate a walkthrough. If "normal" answers are given, they are recorded in the database 24. The patient interface module 534 does not make decision about what questions to ask. This is done by the walkthrough interface module 538. The patient interface module 534 asks the walkthrough interface module 538 for Question #1. Once it gets the question, the patient interface module 534 asks the user that question through the voice generator 22, in Step C1. Then the patient provides an answer, which is read through the DTMF interface 532 in Step C2. Finally, the answer is given to the walkthrough interface module 538 in Step C3, which makes use of the answer and provides the patient interface module 534 with another question to ask.

This architecture may seem complex, but the goal is to reduce the complexity and generality of each module. This facilitates changes in modules that may be required when the system is updated or modified. In alternative embodiments, different module configurations may be used.

The patient login scheduling module 536 determines which walkthrough(s) each patient must go through. The health care provider can of course modify the schedule using a provider interface 540. Some patients must go through more than one walkthrough.

The provider interface 540 is a complex GUI that makes it easy for the health care providers and administrator to access the database system. They can configure their own screens for data entry and display using a screen interface module 542. They can configure their own reports using a report module 544. They can configure walkthroughs using the walkthrough interface module 538. Of course, the system will come ready with several reports, screens, and walkthrough, so many providers will not need to create any additional interface screens, reports, or walkthroughs at all.

The screen interface module 542 stores and displays GUIs to data entry and data display from the database 24. Graphical User Interfaces (GUIs) are standard to the industry, and thus need not be described in detail here. The provider interface 540 can ask for a particular screen to be displayed. It is also possible through the provider interface 540 to create new screens and modify existing ones.

The walkthrough interface module 538 controls the walkthroughs, and the patient's journey through them. The walkthrough interface module 538 gives questions to the patient interface module 534 to ask the patient, and receives answers from the patient interface module 534. In place of an answer, the walkthrough interface module 538 may receive a "no key pressed" or "hangup" response. The walkthrough interface module 538 remembers what question was asked most recently, and thus knows or can determine, which is the next question to ask. The walkthrough interface module 538 is in charge of sending answers to the database 24 to be stored. It can also be told to print a special report by using the report module 544.

The following procedure describes part of the walkthrough interface module 538.
Handle One Question and Answer This procedure is called by either the Provider Interface 540 or the Patient Interface 534. It goes through each step of a walkthrough, asking questions and getting answers. This procedure uses a variable "LAST QUESTION" which records the last question asked of the patient.

A. Get "answer" from the Provider Interface 540 or Patient Interface 534

B. If there is no "LAST QUESTION" then:
Set "LAST QUESTION" to question #1.
Return question #1.

C. Otherwise,
1. This data is the answer to the "LAST QUESTION"
2.
   a. Record the data, if appropriate.
   b. Generate the next question for this patient, if appropriate.
3. If there is a next question for this patient:
   a. Set "LAST QUESTION" to be the next question
   b. Return this question
4. Otherwise, Return that no questions are left to ask The procedure "Handle One Question and Answer" receives the answer to the last question from the patient interface module 534 in Step A. Of course, there is no answer to receive if Question #1 has not been asked yet, which is the case handled in Step B. In that case, the appropriate response is to ask Question #1. This question is "remembered" so that when an answer is received, it can be matched with Question #1. If this is not the first question, then in Step C, the answer received is matched with the last question asked, stored in a variable. This answer may be recorded in the database 24, or may cause a report to be printed out. In StepC2b, a new question is generated and passed to the patient interface module 534, in Step 3.

The report module 544 performs queries on the database 24 and produces reports. Reports may be printed out for a provider to read or for record keeping. Reports may be stored on-line for future reference, or may be sent to a provider directly, for example, by email. The provider or administrator may create a new report or modify an existing report using the report module 544 through the provider interface 540.

The Server/Client Communication 550 is, in the representative embodiment, a local area network (LAN) that allows the interface server 530 to talk with the database server 560. It is possible that these two servers are actually running on the same computer, and possibly as part of the same program, in which case there is no need for the Server/Client Communication 550.

The database 24 should have an interface that is simple to understand. The Database Interface Language 562 provides a way for programmers to create queries and have them run as small interpreted programs. Database languages are standard to the state of the art in databases. The "Database Interface Language" 562 asks a Security module 564 to validate all requests.

The database 24 should force users to identify themselves to protect the database 24 from unauthorized accesses and additions.

The database 24 actually stores the data. Because it is controlled through an easy to use "Database Interface Language" 562, the database 24 itself can be quite complex. Allowing complexity also allows the database 24 to be high performance, or distributed across several hard drives. The database 24 utilizes the computer's underlying operating system 566 to store all files.

Other modules that can be incorporated into the central monitoring subsystem 11 include a medical questions and forms file, a patient billing subsystem, a database table of health care providers, a drug database and compliance subsystem, an expert system with rules for diagnosis, treatments and alerts, and an electronic mail system.

Accordingly, the software of central monitoring system 11 of the present invention has the capability of: identifying the patient or health care provider and invoke the appropriate security checks; retrieving patient records; activating an expert system that determines what questions to ask the patient; activating the expert system to evaluate a patient's responses; if appropriate, activating drug compliance and recommendations files; making recommendations to the patient and the health care provider; recording patient usage and/or billing; and forwarding appropriate reports and alerts to the health care provider.

In an alternative embodiment, the outpatient subsystem 12 can include a personal computer coupled to the telecommunications system 13 by a modem, so as to enable modem to modem communication between a patient and the central monitoring subsystem 11. (This embodiment is particularly useful for patients having a hearing problem.)

The central monitoring subsystem 11 can be coupled to the telecommunications system 13 over a PBX (Public Branch Exchange).

The computer processor 21 can be a plurality of computer processors, such as high-end personal computers with 486 chips, coupled together as a local area network. Preferably, there would be separate network and data servers. For example, once a patient's access code is decoded, that patient's file could be batch loaded from the data server into the local PC memory, and the PC would handle all of the interactions with the patient, freeing the network. (In fact, a single PC could handle more than one patient call simultaneously.) Some of the data stored could be stored on CD-ROM resident in each PC. The CD-ROMs could store digitized sound bytes and the PCs could use a local multimedia sound card to reply to the calling patient. This could allow, for example, the use of a simpler voice mail-type system (that often is bundled with large PBX systems) to give the patient or provider access.

Optionally, the central monitoring subsystem 11 has capabilities for: electronic mail interfaces to allow questions or queries by users; management of telecommunications ports to insure access by all users; and regular backup of patient files.

Figure 6:
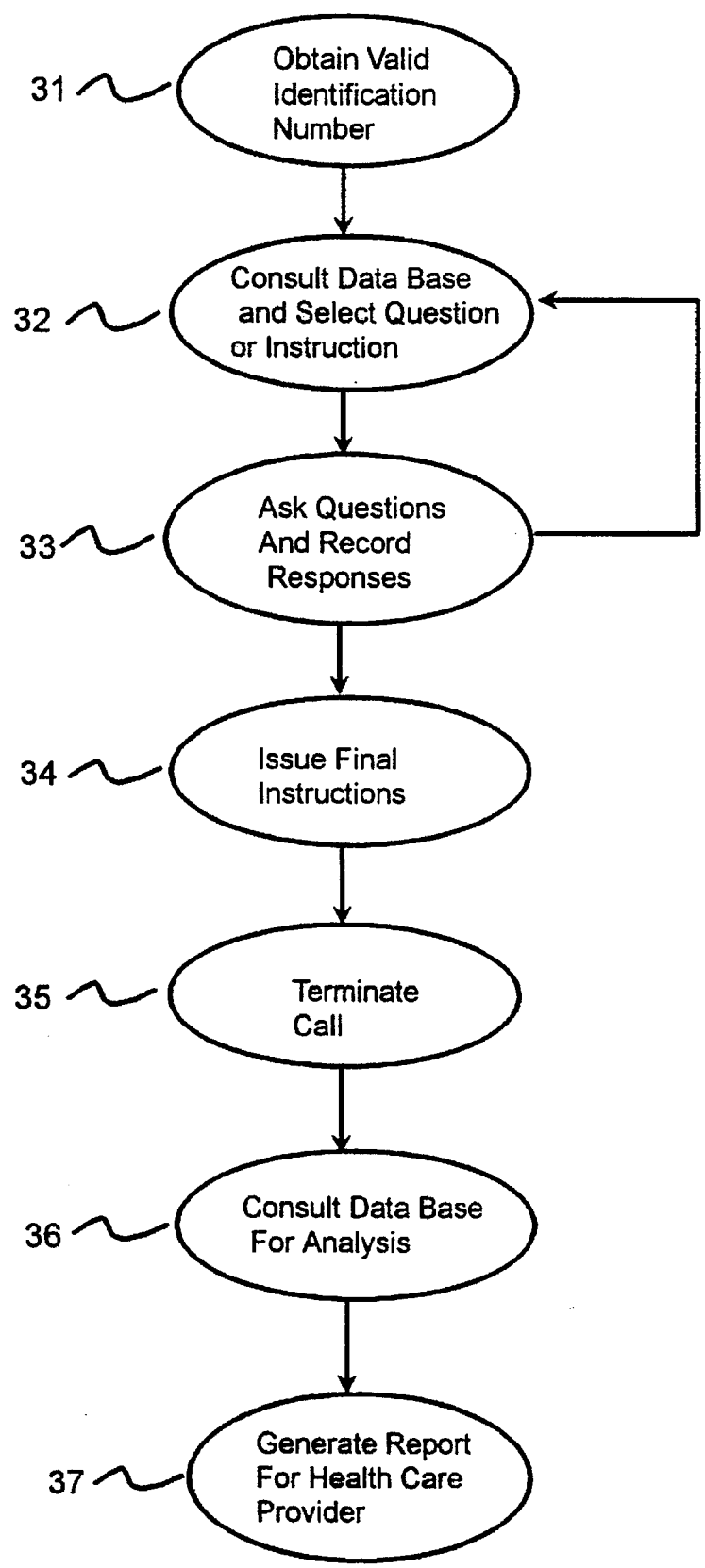
FIG. 6 is a diagram in flow chart form of a method of operating a representative embodiment of the present invention.

FIG. 6 describes in flow chart form typical steps used in the operation of a representative embodiment of the present invention. A patient utilizes the invention by dialing a telephone number supplied by the health care provider using a touch tone telephone. The modem 23 is coupled to a telephone line. (There may be more than one modem coupled to the processor 21, allowing more than one call to be handled at the same time.)

The modem 23 answers the incoming telephone call and, under the control of the computer processor and utilizing the voice generator 22, directs the patient to enter his or her personal identification number (PIN) using the appropriate keys on the touch tone keypad of the patient's telephone. The modem 23 decodes the information received from the patient, and passes this information to the computer processor 21 (step 31). The computer processor 21, after checking the database 24 to determine if the entered PIN is valid, retrieves the correct patient record.

If the PIN is not entered correctly, the computer processor 21 requests the patient to retry entering the PIN. If the computer processor 21 is unable to recognize a valid PIN after a predetermined number of consecutive failed attempts by the patient, the computer processor 21 terminates the call.

Upon accepting a valid PIN, the computer processor 21 consults the retrieved patient record and the database 24 to select one or more appropriate questions for the patient to respond to (step 32).

The computer processor 21, via the voice generator 22 and the modem 23, proceeds to ask the patient a question and instructs the patient how to transmit an answer. The patient transmits an answer, and the DTMF modem 23 translates the answer into a form recognizable by the computer processor 21 (step 33). The answer received from the patient can be stored in that patient's record in the database.

The computer processor 21 will select the next question, if any, for example by consulting the database 24 along with the patient's response to a prior question or questions. If the computer processor 21 decides that no further questioning is necessary, it will issue final instructions (step 34), if any, to the patient and then terminate the call (step 35).

After the call is terminated, the computer processor 21 will consult the database 24 (step 36), and immediately or at predetermined intervals, generate one or more reports for the health care provider (step 37). The reports are based on the patient's record in the database 24, including the answers to the questions received from the patient at the central monitoring subsystem 11. Typically, the reports are generated at the output device 25.

Attached hereto as Appendix A, and expressly incorporated herein, is pseudo-code illustrating a representative algorithm that can be used to control the operation of the computer processor 21 of the present invention.

The present invention can be used to monitor a patient's health condition whilst undergoing treatment and to monitor the health of people who have (or who are susceptible to) certain medical conditions, such as, for example, prostrate cancer, heart disease or arthritis. Accordingly, the system of the present invention can be used to monitor patients with chronic diseases, such as, for example, post MI, cancer, arthritis, diabetes, and the like. The monitoring can be of a patient's subjective and emotional state (e.g., how the patient "feels") and of the patient's physical condition (e.g., blood glucose levels).

The present invention can also be used to assist in the diagnosis of medical conditions as well as for monitoring treatment. Thus, the present invention can be used to monitor the health status of a healthy person, so that if there is a change in that person's condition, a doctor or other health professional will be alerted by the central monitoring subsystem 11. Moreover, the information entered by the person at the outpatient subsystem 12 and stored at the central monitoring subsystem 11 can be used to assist in the diagnosis of the medical condition or illness.

The present invention can be used to monitor and report side effects of drugs prescribed to a patient. When the health care provider determines, based upon the information entered by the patient and stored in the patient's record in the database 24, that the patient is being adversely effected by a prescribed drug, the health care provider can contact the patient (or have the central monitoring subsystem 11 alert the patient on the patient's next call or call the patient back) and reduce the dose of the medication or change the medication to reduce the side effect.

Another use of the present invention is to monitor patient compliance. Often when a patient is prescribed a drug, the patient does not complete the full course of treatment, fails to take the required dose at the required time, or fails to take the drug at all. Using the system of the present invention, a health care provider or drug company can monitor whether the patient is taking the required dose of a drug at the correct times. The system of the present invention can be configured so that a patient reports regularly (for example, each day) as to the amount and time that a particular drug was taken. Additionally, the central monitoring subsystem 11 can remind a patient when a patient calls of the need to take the correct dosage at the correct time, of what the correct dosage is, the conditions under which the drug should be taken (e.g., with milk, before food etc.), the side effects (e.g., drowsiness, so do not drive etc.) and the benefits of taking the drug. In an advanced embodiment, the central monitoring subsystem 11 can itself call the patient if the patient has not reported within a set period of time and remind the patient (using the voice generator 22) of the need and benefits of taking the prescribed drug.

Reporting of patient compliance with respect to the taking of drugs using the system of the present invention has many advantages. The patient is constantly reminded of the need to take the drug, and when making a report to the central monitoring subsystem 11, is educated on an on-going basis as to, for example, the advantages of the drug and the proper way to take the drug. Additionally, this compliance feature can be is used in conjunction with the patient reporting (as discussed above) as to the side effects of the drug and as to the patient's physical and mental condition whilst taking the drug. The health care provider is thus kept informed as to the patient's progress, both as to health and compliance. Moreover, the information entered by the many patients who are prescribed a drug (compliance, health status, side effects, etc.) creates an extremely valuable database of information for pharmaceutical companies, for example, as to the positive and negative effects of the drug, the time to recovery, patient outcomes and the overall success of the medication. Thus, the database 24 can also be used to store outcome information relating to one or more drugs. This information can be stored separately from the patient records.

Additionally, the present invention can be used to monitor the interactions between drugs, for example, when a patient is taking two or more drugs.

The patient record created using the monitoring system of the present invention is updated at regular intervals by the patient. This patient record, which is stored in the database 23, is an excellent record that a doctor or health care provider can use when performing a diagnosis. For example, when a doctor is examining a patient, it is usually important to take a medical history of the patient. The doctor will often ask the patient how he or she feels and how he or she felt in the past one or two weeks. Most patients cannot remember when and how they felt on particular days in the past, and what the exact symptoms they were suffering from were at any particular time. If a person uses the system of the present invention to report regularly to the central monitoring subsystem 11, a doctor will have a continuous record (created contemporaneously by the patient) of the patient's condition at regular periods in the past. This record is extremely helpful in diagnosis.

The present invention can be used for screening purposes by a health care provider. The information entered by a patient can be analyzed by the health care provider to determine which patients have chronic or acute conditions that require an immediate personal consultation.

The present invention can also be used to allow patients to make an appointment with the health care provider.

An important part of health is diet. The present invention can be used to monitor a patient's diet. For example, the patient can call in using the outpatient monitoring subsystem 12, such as, for example, a touch-tone telephone, and answer questions provided by the central monitoring subsystem 11 as to what and how much the patient has eaten that day. The central monitoring subsystem 11 can then calculate and inform the patient as to the number of calories that patient has consumed. The patient can be informed by the central monitoring subsystem 11 as to the best food groups to eat, and of suggested modifications to diet. This aspect of the present invention is particularly useful for people trying to lose weight.

Many people do not live close to a health care provider. The present invention can be used to monitor the health of people living in rural areas. Also, the present invention can be used to monitor the health of underserved poor who find it difficult to visit a doctor regularly, but who have easy access to a telephone.

For certain medical conditions, it is suggested that patients use the system of the present invention in between regular visits to the health care provider. In certain circumstances, the patient may not be truthful when answering questions according to the system of the present invention. Accordingly, a health care provider should be careful in recommending a change in medication based solely upon a patient's report to the central monitoring subsystem. In a representative embodiment, the expert system that is utilized by the present invention has functionality to help ascertain if a patient is answering questions truthfully and consistently.

When children or other family members are sick, the present invention can be used by the child's parent or other family member. For example, the mother can sit down with the sick child and ask the child questions that are printed on a chart, such as the chart described in U.S. Pat. No. 4,346,697. The mother can then telephone the central monitoring subsystem 11 and report the child's health condition.

The present invention has the capability of providing messages to patients in different languages, such as, for example, Spanish or French. Different telephone numbers could be allocated to patients who understand different language so that the central monitoring subsystem will "know" in which language to provide messages to the patient. Alternatively, the patient could be given the option, when first connecting with the central monitoring subsystem, of changing the language of the messages.

The principles of the present invention can be used to also monitor the health and welfare of family pets and farm animals.

EXAMPLE ONE

An outpatient measures his body temperature and blood pressure at home and then uses a touch tone telephone to call a central monitoring subsystem 11 that is located in a hospital. Once connected, the computer processor 21 of the central monitoring subsystem 11 actuates the voice generator 22 and asks the outpatient to enter a PIN. Accordingly, the outpatient enters his PIN, e.g., "234165" using the keys of his telephone keypad.

Once the identification number is accepted, the computer processor 21 asks the patient to enter the outpatient's body temperature on the touch tone keypad. Assuming the temperature of the patient is 98 degrees, the outpatient presses the "nine" key; then the "eight" key. By so doing, the outpatient tells the computer processor 21 that the outpatient has measured the outpatient's body temperature to be 98 degrees Fahrenheit.

The computer processor 21, actuating the voice generator 22, asks the outpatient if the outpatient intended to enter a body temperature of 98 degrees Fahrenheit. The computer processor 21 instructs the outpatient to press the "one" key if the answer is yes, and the "two" key if the answer is no. If the outpatient presses the "one" key, the computer processor 21 records the 98 in the database 24 as the patient's temperature on that day at that time, and proceeds to the next question.

The computer processor 21 next asks the outpatient to enter the outpatient's systolic blood pressure on the outpatient's touch tone keypad. The outpatient touches the keys "one", then "two", and then "five". The computer processor 21 confirms that the outpatient intended to enter one hundred twenty five as a systolic blood pressure and enters the number in the database 24.

The computer processor 21 asks the outpatient to enter the outpatient's diastolic blood pressure on the outpatient's touch tone keypad. The outpatient touches the keys "seven" and then "zero". The computer processor 21 confirms that the outpatient intended to enter seventy five as a systolic blood pressure and records the number in the database 24.

The computer processor may ask other questions as may be necessary. For example, the outpatient may be asked to enter information relating to mood, how well the patient slept, appetite, energy, enjoyment of the day and the like. It is noted that the present invention can be used to monitor the general health of people who are not currently undergoing treatment.

The computer processor 21 can record additional information in a database 24, such as the time and date of the telephone call.

The computer processor 21 can, using the DBMS program, query the database 24 and analyze the information received. Assume that the health care provider entered information in the database 24 at an earlier date pertaining to the outpatient. The information indicates that the outpatient's medication should be discontinued if the outpatient's systolic blood pressure falls below one hundred thirty, but only if the outpatient's body temperature is less than one hundred degrees at the same time. Further, the information indicates that the health care provider be informed of the occurrence of these conditions.

Thus, a report is generated so that the health care provider is altered to this fact, and can make a decision as to whether to telephone the patient regarding his medication or whether the patient should come in for an appointment.

Alternatively, the present invention can be configured so the voice generator 22, under the control of the computer processor 21, instructs the outpatient to stop taking his medication and terminates the call. In such a case, the computer processor 21 generates a report using the output device 25 detailing the time and date of the call, the patient's body temperature and blood pressure, and the instructions delivered to the patient. The computer processor 21 can mark the report "URGENT—READ BY [Time] [Date]".

EXAMPLE TWO

The patient may be afflicted by maladies and, in particular, by depression. The patient is provided with a symptom chart of the type described in U.S. Pat. No. 4,346,697. Upon completion of the symptom chart for a specific period, the patient is instructed to call by telephone the physician's telephone number that will connect the patient's telephone to the central monitoring subsystem 11. The patient enters his PIN using the keys of the touch tone keypad, and will respond to the predetermined questions on his chart regarding his condition during this period of time. The following is an example of the questions that the central monitoring subsystem 11 asks the patient to respond as follows:

A. MEDICATION:
Patient is asked if he/she has taken prescribed medication. If answer is YES, press the number "1"; if answer is NO, press the number "2".
B. MY MOOD TODAY:
Patient is prompted . . . If you are
Happy most of the time, Press "1"
Happy more than sad or blue, Press "2"
Sad or blue more than happy, Press "3"
Sad or blue most of the time, Press "4"
Sad or blue all of the time, Press "5"
So sad I couldn't stand it, Press "6"
C. MY FEELINGS OF ANXIETY TODAY:
Patient is prompted . . . If you are
Not anxious, tense or fearful, Press "1"
Occasionally anxious, tense or fearful, Press "2"
Very anxious, shaky, or jittery inside, Press "3"
Very anxious, tense, or fearful most of the day, Press "4"
So anxious, my hands or legs were actually shaking, Press "5"
Terrified or panicky most of the day, Press "6"
(Patient continues responding to the remaining sections D through I).
J. Deals with other specific symptoms that may have occurred during this same period of time. For example,
Patient is prompted . . . If you
Fell down, Press "1"
Felt faint, Press "2"
Unsteady walking, Press "3"
Trouble urinating, Press "4" . . .
. . . and so on through seven additional symptoms.

APPENDIX A

| | | |
|---|---|---|
| (A11) | Receive call from patient | |
| (A12) | Ask patient for valid identification number | |
| (A13) | Record valid identification number p | |
| (A14) | Set integer m = 1 | /* m is an index for counting the current number of invalid responses given by the patient */ |
| (A15) | While (invalid number entered and m < n) do /* n is a preset maximum for invalid responses, after which the call will be terminated */ | |
| (A16) | Ask patient for valid identification number | |
| (A17) | If (number is valid) | |
| (A18) | Record valid identification number p | |
| (A19) | End if | |
| (A20) | Increment m | |
| (A21) | End while | |
| (A22) | If (m = n) | |
| (A23) | Terminate call | |
| (A24) | End if | |
| (A25) | set integer l = 0 | /* l is a flag returned by subroutine NextQuestion; when l=0, there is another question to be asked. When l=1, there are no more questions to be asked. */ |
| (A26) | While (l = 0) do | |
| (A27) | FirstQuestion(p,j) | /* FirstQuestion is a subroutine that imports valid patient identification number p and exports first question number j */ |
| (A28) | Ask question number j | /* j is an integer corresponding to a question stored in a database that can be asked of a patient */ |
| (A29) | Give response options | |
| (A30) | Receive response r | |
| (A31) | Set integer m = 1 | |
| (A32) | While ((response is not a valid option) and (m < n)) do | |

-continued

APPENDIX A

| | |
|---|---|
| (A33) | Indicate invalid choice |
| (A34) | Re-ask question |
| (A35) | Give response options |
| (A36) | Receive response r |
| (A37) | Increment m |
| (A38) | End while |
| (A39) | If (m = n) |
| (A40) | Terminate call |
| (A41) | End if |
| (A42) | Write Record(j,r) |
| (A43) | Call NextQuestion(j,r,k,l) |
| | /* NextQuestion is a subroutine that imports the current question number (j) along with the response given by the patient (r). The subroutine selects the next question k based upon j and r, and exports integer k to the main program. When there are no further questions, the subroutine sets flag l=1 and exports it to the main program, which terminates the call. */ |
| (A44) | set integer j = k |
| (A45) | End While |
| (A46) | Deliver final instructions or message to patient |
| (A47) | Terminate call |
| (A48) | Call ReportMaker(Record(x,y)) |
| | /* ReportMaker is a subroutine that imports the questions asked along with their answers and generates a report for the health care provider */ |
| (A49) | Await the next call |

What is claimed is:

1. A patient-initiated patient monitoring system, comprising:

a touch-tone telephone having a plurality of keys operated by a patient to generate DTMF tones, the DTMF tones representing a health condition of the patient, the patient utilizing the touch-tone telephone to initiate an interactive health care communication session at a time convenient to the patient by calling a central monitoring system; and a central monitoring system coupled via a communications system to the touch-tone telephone for interacting with the patient during the interactive health care communication session, the central monitoring system not initiating communications with the patient and wherein such interactive health care communication sessions are initiated by the patient rather than the central monitoring system, the central monitoring system answering the call initiated by the patient at the touch-tone telephone, in response thereto the central monitoring system generating a plurality of questions concerning the health condition of the patient for the patient to answer using the plurality of keys of the touch-tone telephone, and storing answers to the plurality of questions for later retrieval, the central monitoring system including a DTMF modem decoder receiving and decoding the DTMF tones generated by the patient using the touch-tone telephone and transmitted over the communications system to the central monitoring system, a computer processor coupled to the DTMF modem decoder, a voice generator coupled to the computer processor generating voice output under the control of the computer process, said voice output transmitted over the communications system to the touch-tone telephone, a database coupled to the computer processor storing a patient record representing the health condition of the patient and storing the plurality of questions concerning the health condition of the patient, wherein the computer processor retrieves the plurality of questions concerning the health condition of the patient from the database and causes the voice generator to generate voice output representing the plurality of questions, and wherein the patient responds to the plurality of questions using the plurality of keys of the touch-tone telephone to generate DTMF tones representing the health condition of the patient, the DTMF tones decoded by the DTMF modem decoder, the computer processor storing information concerning the health condition of the patient in the patient record.

2. The patient monitoring system of claim 1 further comprising a database management system coupled to the database to access the database and generate reports representing the health condition of the patient.

3. The patient monitoring system of claim 2 further comprising a printer coupled to the central monitoring system to print the reports generated by the database management system.

4. The patient monitoring system of claim 2 further comprising a display screen coupled to the central monitoring system to display the reports generated by the database management system.

5. The patient monitoring system of claim 1 further comprising a printed patient symptom chart comprising the plurality of questions, the patient symptom chart completed by the patient with answers representing the health condition of the patient.

6. The patient monitoring system of claim 1 further comprising a personal computer system with a modem and a display device, the personal computer coupled to the DTMF modem decoder via the communications system, the personal computer system operatable by the patient to report the health condition of the patient to the central monitoring system.

7. The patient monitoring system of claim 6 further comprising a patient symptom chart comprising the plurality of questions, the patient symptom chart displayed on the display device of the personal computer system, the patient symptom chart completed by the patient with answers representing the health condition of the patient, wherein the answers representing the health condition of the patient are transmitted to the central monitoring system over the communications system.

8. A patient-initiated drug compliance system to monitor compliance by a patient in taking prescribed drugs, comprising:

a touch-tone telephone having a plurality of keys operated by a patient to generate DTMF tones and enabling the patient to initiate a monitoring session between the patient and a central monitoring system at a time convenient to the patient, wherein such monitoring session is exclusively initiated by the patient; and a central monitoring system coupled via a telecommunications system to the touch-tone telephone, the central monitoring system not initiating communications with the patient but instead awaiting initiation of the monitoring session by the patient, the central monitoring system generating a plurality of questions concerning compliance by the patient in taking prescribed drugs for the patient to answer using the plurality of keys of the touch-tone telephone, and storing answers to the plurality of questions for later retrieval, the central monitoring system including a DTMF modem decoder receiving and decoding the DTMF tones generated by the patient using the touch-tone telephone and transmitted over the telecommunications system to the central monitoring system, the DTMF tones representing compliance by the patient in taking a prescribed drug, a computer processor coupled to the DTMF modem decoder, a voice generator coupled to the computer processor generating voice output under the control of the computer process, said voice output transmitted over the telecommunications system to the touch-tone telephone, a database coupled to the computer processor storing a patient record reflecting compliance by the patient in taking the prescribed drug and storing the plurality of questions concerning compliance by the patient in taking the prescribed drug, wherein the computer processor retrieves the plurality of questions concerning compliance by the patient in taking the prescribed drug from the database and causes the voice generator to generate voice output representing the plurality of questions, and wherein the patient responds to the plurality of questions using the plurality of keys of the touch-tone telephone to generate DTMF tones representing the compliance by the patient in taking the prescribed drug, the DTMF tones decoded by the DTMF modem decoder, the computer processor storing information concerning compliance by the patient in taking the prescribed drug in the database.

9. The drug compliance system of claim 8 further comprising a database management system coupled to the database to access the database and generate reports representing compliance by the patient in taking the prescribed drug.

10. The drug compliance system of claim 9 further comprising a printer coupled to the central monitoring system to print the reports generated by the database management system.

11. The drug compliance system of claim 9 further comprising a display screen coupled to the central monitoring system to display the reports generated by the database management system.

12. A patient monitoring system, comprising:

a touch-tone telephone having a plurality of keys operated by a patient to generate DTMF tones, the DTMF tones representing a health condition of the patient; and a central monitoring system coupled via a communications system to the touch-tone telephone, the central monitoring system generating one or more questions concerning the health condition of the patient for the patient to answer using the plurality of keys of the touch-tone telephone, and storing answers to the one or more questions for later retrieval, the central monitoring system including a DTMF modem decoder receiving and decoding the DTMF tones generated by the patient using the touch-tone telephone and transmitted over the communications system to the central monitoring system, a computer processor coupled to the DTMF modem decoder, a voice generator coupled to the computer processor generating voice output under the control of the computer process, said voice output transmitted over the communications system to the touch-tone telephone, a database coupled to the computer processor storing a patient record representing the health condition of the patient, and processing means for generating the one or more questions concerning the health condition of the patient, said processing means utilizing information in the patient record and any previously received patient answers to dynamically generate the one or more questions;

wherein the computer processor causes the voice generator to generate voice output representing the one or more questions generated by the processing means, and wherein the patient responds to the one or more questions using the plurality of keys of the touch-tone telephone to generate DTMF tones representing the health condition of the patient, the DTMF tones decoded by the DTMF modem decoder, the computer processor storing information concerning the health condition of the patient in the patient record.

13. The patient monitoring system of claim 12 wherein the processing means includes an expert system.

14. A computer-based system including an automated central monitoring system to report health status of a patient to a health care provider, the system comprising:

means for remotely accessing the central monitoring system;

means for transmitting patient identification information in voice form to the central monitoring system;

means, located at the central monitoring system, for receiving the patient identification information, and for comparing the patient identification information with previously stored voice fingerprints so to securely identify the patient;

means for retrieving a record for the identified patient;

means, located at the central monitoring system, for utilizing the record and previously received patient responses to dynamically generate a plurality of questions relating to a health condition of the patient;

means, located at the central monitoring system, for transmitting, in voice generated form, the plurality of questions relating to the health condition of the patient to the patient;

means for entering a response to each of the plurality of questions relating to the health condition of the patient;

means for transmitting each response to the central monitoring system; and means, located at the central monitoring system, for receiving and decoding each response and thereafter storing each response in the record.

15. A computer-based patient-initiated method to allow the reporting of health status of a patient to a computerized and automated central monitoring system, the central monitoring system including a computer processor, the method comprising the steps of:

at the central monitoring system, not initiating communications with the patient but instead awaiting for the patient to initiate a health status communication session between the patient and the central monitoring system;

at a time convenient to the patient, initiating the health status communication session by remotely accessing the central monitoring system with a touch-tone telephone having a plurality of keys, wherein such health status communication session is exclusively initiated by the patient;

entering, using the plurality of keys on the touch-tone telephone, a patient identification number;

transmitting the patient identification number as DTMF tones to the central monitoring system;

at the central monitoring system, receiving and decoding the patient identification number;

at the central monitoring system, retrieving a record corresponding to the patient identification number;

at the central monitoring system, utilizing the record to generate a plurality of questions relating to a health condition of the patient;

transmitting, in voice generated form, the plurality of questions relating to the health condition of the patient to the touch-tone telephone;

at the touch-tone telephone, entering a response to each of the plurality of questions relating to the health condition of the patient;

transmitting each response as DTMF tones to the central monitoring system; and at the central monitoring system, receiving and decoding each response and thereafter storing each response in the record.

16. The method of claim 15 further comprising the step of periodically generating, at the central monitoring system, a report relating to the health condition of the patient.

17. The method of claim 15 wherein the step of utilizing the record to generate a plurality of questions relating to a health condition of the patient comprises the step of interactively utilizing each response received at the central monitoring system to generate a question relating to the health condition of the patient.

18. The method of claim 15 wherein a plurality of patients access the central monitoring system concurrently.

19. The method of claim 15 further comprising the initial steps of:

administering to the patient a patient-completable symptom chart comprising a plurality of symptom fields;

completing the patient completable symptom chart with information concerning at least one symptom; and reporting to the central monitoring system the information completed by the patient on the patient-completable symptom chart.

20. The method of claim 15 wherein the plurality of questions relating to the health condition of the patient include questions relating to drug compliance.

21. The method of claim 15 wherein the plurality of questions relating to the health condition of the patient include questions relating to diet.

22. The method of claim 15 wherein the plurality of questions relating to the health condition of the patient include questions relating to a psychological illness.

23. The method of claim 15 wherein the plurality of questions relating to the health condition of the patient include questions relating to depression.

24. The method of claim 15 wherein the plurality of questions relating to the health condition of the patient include questions relating to vital signs.

25. The method of claim 15 wherein a plurality of patients access the central monitoring system and wherein the plurality of questions generated for a first patient are different than the plurality of questions generated for a second patient.

26. The method of claim 15 further comprising the steps of:

processing each response received; and altering a medication of a drug prescribed to the patient.

27. The method of claim 15 further comprising the steps of:

remotely accessing the central monitoring system with a personal computer having a modem;

entering, using the personal computer, a second patient identification number;

transmitting the second patient identification number via the modem to the central monitoring system;

at the central monitoring system, receiving the second patient identification number;

at the central monitoring system, retrieving a second record corresponding to the second patient identification number;

at the central monitoring system, utilizing the second record to generate a second plurality of questions relating to a health condition of a second patient;

transmitting the second plurality of questions relating to the health condition of the second patient to the personal computer;

at the personal computer, entering a response to each of the second plurality of questions relating to the health condition of the second patient;

transmitting each response via the modem to the central monitoring system; and at the central monitoring system, receiving and decoding each response and thereafter storing each response in the second record.

28. A computer-based method to report health status of a patient to a computerized central monitoring system, the central monitoring system including a computer processor, the method comprising the steps of:

remotely accessing the central monitoring system with a touch-tone telephone having a plurality of keys;

at the central monitoring system, retrieving a record for the patient;

at the central monitoring system, utilizing the record and previously received responses to dynamically generate a plurality of questions relating to a health condition of the patient;

transmitting, in voice generated form, the plurality of questions relating to the health condition of the patient to the patient;

at the touch-tone telephone, entering a response to each of the plurality of questions relating to the health condition of the patient;

transmitting each response as DTMF tones to the central monitoring system;

at the central monitoring system, receiving and decoding each response and thereafter storing each response in the record;

at the central monitoring system, processing each response received; and immediately alerting a health care provider if the patient requires emergency medical treatment.

29. A patient-initiated system for monitoring the health of a patient and enabling patients to initiate monitoring sessions when convenient to the patient and without initial communication from a central system, comprising:

a patient communications device for initiating a monitoring session at a time convenient to the patient and for thereafter receiving as input from the patient health information and for transmitting the health information over a communications system; and a central monitoring system coupled via the communications system to the patient communication device, the central monitoring system not initiating communications with the patient but instead awaiting initiation of a monitoring session by the patient and thereafter generating a plurality of questions concerning a health condition of the patient for the patient to answer using the patient communications device, and storing answers to the plurality of questions for later retrieval, the central monitoring system including a decoder receiving and decoding the health information input by the patient and transmitted by the patient communications device over the communications system to the central monitoring system, a computer processor coupled to the decoder, means, coupled to the computer processor, for generating output messages understandable to the patient under the control of the computer processor, said output messages transmitted over the communications system to the patient communications device, a database coupled to the computer processor storing a patient record representing the health condition of the patient and storing the plurality of questions concerning the health condition of the patient, wherein the computer processor retrieves a subset of the plurality of questions concerning the health condition of the patient from the database and causes the means for generating output messages to generate output messages representing the subset of the plurality of questions, and wherein the patient responds to the plurality of questions using the patient communications device which transmits the health information to the decoder, the decoder decoding the health information, the computer processor storing corresponding information concerning the health condition of the patient in the patient record.

30. A computer-based method to report health status of a patient to a computerized central monitoring system, the central monitoring system including a computer processor, the method comprising the steps of:

remotely accessing the central monitoring system with a touch-tone telephone having a plurality of keys;

at the central monitoring system, retrieving a record for the patient;

at the central monitoring system, utilizing the record and previously received responses to dynamically generate a plurality of questions relating to a health condition of the patient;

transmitting, in voice generated form, the plurality of questions relating to the health condition of the patient to the patient;

at the touch-tone telephone, entering a response to each of the plurality of questions relating to the health condition of the patient;

transmitting each response as DTMF tones to the central monitoring system;

at the central monitoring system, receiving and decoding each response and thereafter storing each response in the record;

processing each response received; and automatically alerting a health care provider if the patient requires an appointment.

31. A computer-based patient-initiated method to report health status of a patient to a computerized central monitoring system, the central monitoring system including a computer processor, the method comprising the steps of:

remotely accessing the central monitoring system with a touch-tone telephone having a plurality of keys;

at the central monitoring system, retrieving a record for the patient;

at the central monitoring system, utilizing the record and previously received responses to dynamically generate a plurality of questions relating to a health condition of the patient;

transmitting, in voice generated form, the plurality of questions relating to the health condition of the patient to the patient;

at the touch-tone telephone, entering a response to each of the plurality of questions relating to the health condition of the patient;

transmitting each response as DTMF tones to the central monitoring system;

at the central monitoring system, receiving and decoding each response and thereafter storing each response in the record;

processing each response received; and automatically alerting the patient at the touch-tone telephone if the patient requires an appointment.

32. The method of claim 31 further comprising the step of allowing the patient to make the appointment utilizing the keys of the touch-tone telephone.

33. A patient-initiated patient monitoring system, comprising:

a touch-tone telephone having a plurality of keys operated by a patient to generate DTMF tones, the DTMF tones representing a health condition of the patient, the patient utilizing the touch-tone telephone to initiate an interactive health care communication session at a time convenient to the patient by calling a central monitoring system;

a central monitoring system coupled via a communications system to the touch-tone telephone for interacting with the patient during the interactive health care communication session and wherein such interactive health care communication sessions are initiated by the patient rather than the central monitoring system, and answering the call initiated by the patient at the touch-tone telephone, in response thereto the central monitoring system generating a plurality of questions concerning the health condition of the patient for the patient to answer using the plurality of keys of the touch-tone telephone, and storing answers to the plurality of questions for later retrieval, the central monitoring system including a DTMF modem decoder receiving and decoding the DTMF tones generated by the patient using the touch-tone telephone and transmitted over the communications system to the central monitoring system, a computer processor coupled to the DTMF modem decoder, a voice generator coupled to the computer processor generating voice output under the control of the computer process, said voice output transmitted over the communications system to the touch-tone telephone, a database coupled to the computer processor storing a patient record representing the health condition of the patient and storing the plurality of questions concerning the health condition of the patient; and a printed patient symptom chart comprising the plurality of questions, the patient symptom chart completed by the patient with answers representing the health condition of the patient, wherein the computer processor retrieves the plurality of questions concerning the health condition of the patient from the database and causes the voice generator to generate voice output representing the plurality of questions, and wherein the patient responds to the plurality of questions using the plurality of keys of the touch-tone telephone to generate DTMF tones representing the health condition of the patient, the DTMF tones decoded by the DTMF modem decoder, the computer processor storing information concerning the health condition of the patient in the patient record.

34. A patient-initiated patient monitoring system, comprising:

a touch-tone telephone having a plurality of keys operated by a patient to generate DTMF tones, the DTMF tones representing a health condition of the patient, the patient utilizing the touch-tone telephone to initiate an interactive health care communication session at a time convenient to the patient by calling a central monitoring system;

a central monitoring system coupled via a communications system to the touch-tone telephone for interacting with the patient during the interactive health care communication session and wherein such interactive health care communication sessions are initiated by the patient rather than the central monitoring system, and answering the call initiated by the patient at the touch-tone telephone, in response thereto the central monitoring system generating a plurality of questions concerning the health condition of the patient for the patient to answer using the plurality of keys of the touch-tone telephone, and storing answers to the plurality of questions for later retrieval, the central monitoring system including a DTMF modem decoder receiving and decoding the DTMF tones generated by the patient using the touch-tone telephone and transmitted over the communications system to the central monitoring system, a computer processor coupled to the DTMF modem decoder, a voice generator coupled to the computer processor generating voice output under the control of the computer process, said voice output transmitted over the communications system to the touch-tone telephone, a database coupled to the computer processor storing a patient record representing the health condition of the patient and storing the plurality of questions concerning the health condition of the patient;

a personal computer system with a modem and a display device, the personal computer system coupled to the DTMF modem decoder via the communications system, the personal computer system operatable by the patient to report the health condition of the patient to the central monitoring system; and a patient symptom chart comprising the plurality of questions, the patient symptom chart displayable on the display device of the personal computer system, the patient symptom chart completed by the patient with answers representing the health condition of the patient, said answers representing the health condition of the patient transmitted to the central monitoring system over the communication system, wherein the computer processor retrieves the plurality of questions concerning the health condition of the patient from the database and causes the generation of output representing the plurality of questions, and wherein when the patient responds to the plurality of questions using the plurality of keys of the touch-tone telephone to generate DTMF tones representing the health condition of the patient, the DTMF tones are decoded by the DTMF modem decoder, the computer processor storing information concerning the health condition of the patient in the patient record.

35. A computer-based patient-initiated method to allow the reporting of health status of a patient to a computerized and automated central monitoring system, the central monitoring system including a computer processor, the method comprising the steps of:

administering to the patient a patient-completable symptom chart comprising a plurality of symptom fields;

completing the patient-completable symptom chart with information concerning at least one symptom;

reporting to the central monitoring system the information completed by the patient on the patient-completable symptom chart in a health status communication session;

at the central monitoring system, waiting for the patient to initiate a health status communication session between the patient and the central monitoring system;

at a time convenient to the patient, initiating the health status communication session by remotely accessing the central monitoring system with a touch-tone telephone having a plurality of keys;

entering, using the plurality of keys on the touch-tone telephone, a patient identification number;

transmitting the patient identification number as DTMF tones to the central monitoring system;

at the central monitoring system, receiving and decoding the patient identification number;

at the central monitoring system, retrieving a record corresponding to the patient identification number;

at the central monitoring system, utilizing the record to generate a plurality of questions relating to a health condition of the patient;

transmitting, in voice generated form, the plurality of questions relating to the health condition of the patient to the touch-tone telephone;

at the touch-tone telephone, entering a response to each of the plurality of questions relating to the health condition of the patient;

transmitting each response as DTMF tones to the central monitoring system; and at the central monitoring system, receiving and decoding each response and thereafter storing each response in the record.

* * * * *